United States Patent
Möller et al.

[11] Patent Number: 6,016,441
[45] Date of Patent: Jan. 18, 2000

[54] METHOD OF TESTING OPEN BUT NOT COMPLETELY VISIBLE CAVITIES

[75] Inventors: Thorsten Jens Möller, Kassel; Karl-Aloys Bütefisch, Bovenden, both of Germany

[73] Assignee: Deutsches Zentrum fur Luft-und Raumfahrt E.V., Bonn, Germany

[21] Appl. No.: 09/010,234

[22] Filed: Jan. 21, 1998

[30] Foreign Application Priority Data

Jan. 27, 1997 [DE] Germany .......................... 197 02 851

[51] Int. Cl.[7] ................................................ G01N 21/00
[52] U.S. Cl. .............................................. 600/477; 356/378
[58] Field of Search ................................ 600/310, 322, 600/343, 344, 473, 476, 475, 477; 356/378, 347, 237; 382/141

[56] References Cited

U.S. PATENT DOCUMENTS

| 4,643,514 | 2/1987 | Raviv et al. |
| 5,054,087 | 10/1991 | Carbon et al. ................. 382/1 |
| 5,106,387 | 4/1992 | Kittrell et al. ................. 606/15 |
| 5,305,759 | 4/1994 | Kaneko et al. ................. 128/655 |
| 5,842,995 | 12/1998 | Mahadevan-Jansen et al. |

*Primary Examiner*—Marvin M. Lateef
*Assistant Examiner*—Shawna J Shaw
*Attorney, Agent, or Firm*—Womble Carlyle Sandridge & Rice

[57] ABSTRACT

In a method of testing open but not completely visible cavities (2), light beams (5) with defined intensities are directed into a standardized cavity (2). An intensity distribution of light beams (5) emanating from the standardized cavity (2) is recorded and saved as a standard distribution. The light beams (5) with the defined intensities are also directed into the cavities (2) to be tested. The intensity distributions of reflected light beams (5) emanating from the cavities (2) to be tested are recorded and compared with the standard distribution.

19 Claims, 1 Drawing Sheet

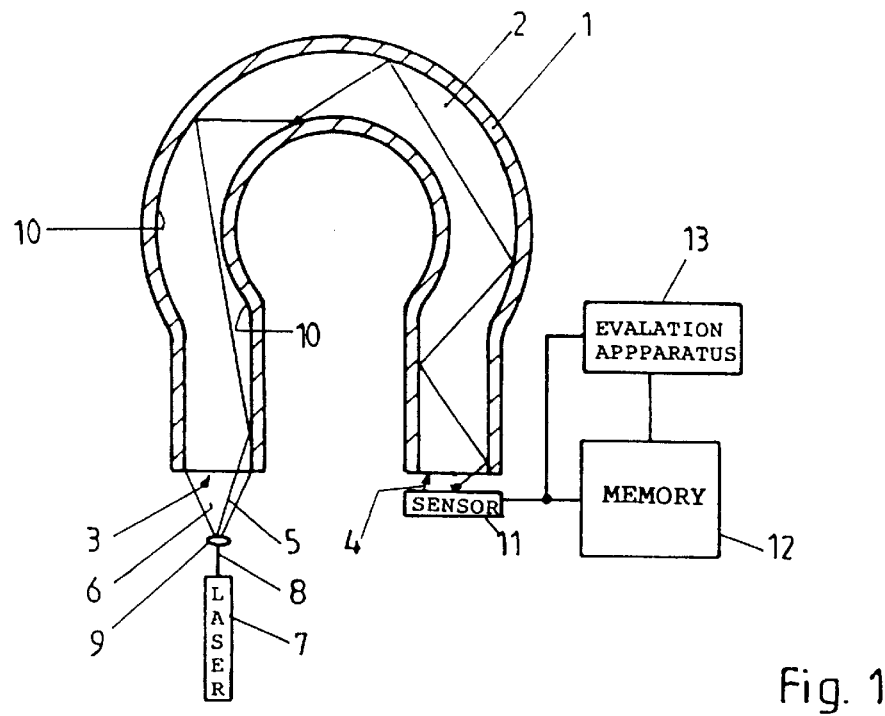
Fig. 1
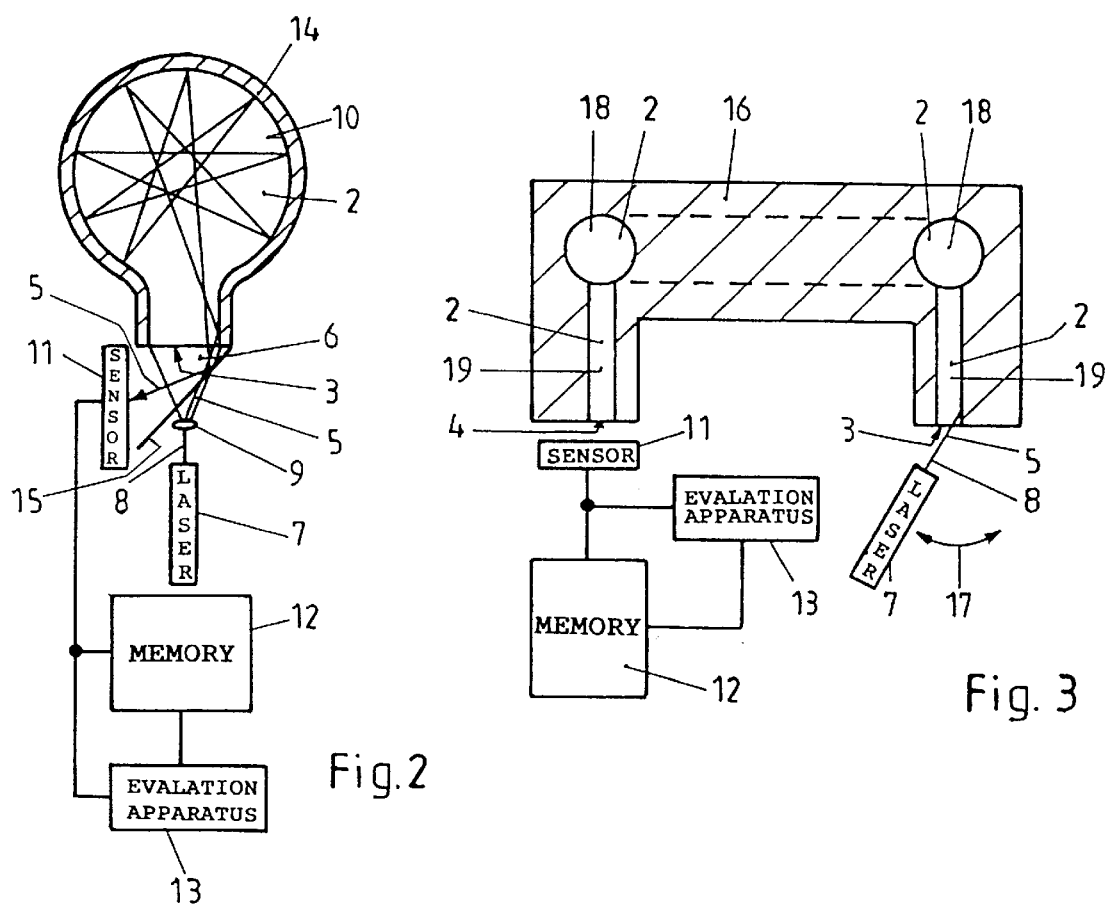
Fig. 2
Fig. 3

METHOD OF TESTING OPEN BUT NOT COMPLETELY VISIBLE CAVITIES

FIELD OF THE INVENTION

The invention is related to a method of testing open but not completely visible cavities. Open but not completely visible cavities are such cavities, in which at least one of their wall regions is not directly visible from the outside through the existing entries into the cavities. In particular, such cavities are referred to, for which penetration into the cavities, for example with an endoscope, would be too expensive for testing the cavities. The cavities can be present in completely different workpieces.

More particularly, the invention deals with the problem of establishing a method of testing non visible cavities, which can be carried out from outside the cavities and does not require inserting instruments into the cavities.

BACKGROUND OF THE INVENTION

A known method of testing open but not completely visible cavities is to take x-ray pictures of the workpieces with the cavities to be tested. But this method requires expensive equipment and is extremely complex.

In addition, it would be feasible to determine the flow resistance of the cavities and to compare it with a standard value. This is, however, only possible if the cavities have two entries so that a flow medium can be directed into one entry and carried off by the other. In addition, flow resistance measurements are very complex since they require a sealed connection of the cavity with the measuring apparatus. Finally, measurable flow resistance is only rarely a criterion for the correct shape of the cavities.

OBJECT OF THE INVENTION

It is the main object of the present invention to establish a method of testing open but not completely visible cavities, which can be applied in a especially rational manner.

SUMMARY OF THE INVENTION

The present invention provides a method of testing open but not completely visible cavities, comprising the steps of directing light beams with defined intensities into a standardized cavity, recording an intensity distribution of light beams emanating from said standardized cavity and saving said intensity distribution as a standard distribution, directing said light beams with said defined intensities into cavities to be tested, recording intensity distributions of light beams emanating from said cavities to be tested, and comparing the recorded intensity distributions with said standard distribution.

In the new method, light beams are used for testing cavities, although the cavities are not completely visible. The light beams are nevertheless capable of detecting non visible areas of the cavities' walls, since they enter and leave these areas through reflection and dispersion on the walls of the cavities, thus yielding information about these areas. This information is utilized by recording the intensity distribution of the light beams emanating from the standardized cavity. The intensity distribution of light beams emanating from the standardized cavity represents those pieces of information which must be available in order to designate the relevant cavity as correct. When the intensity distributions, which have been obtained from the cavities to be tested, are compared with this standard distribution, each difference represents a deviation of the relevant cavity from the standardized cavity. Position and size of the particular differences give information about the type of deviation of the relevant cavity from the standardized cavity.

The light beams directed into the cavities are preferably divergent. This has the effect that the individual light beams are reflected and dispersed on the walls of the cavities in different directions so that all areas of the cavities are detected as uniformly as possible by the light beams.

If the cavities to be tested are lines for fluids of any type, the intensity distribution of light beams emanating from the cavities are preferably recorded at another point of entry into the cavity than that where the light beams have entered the cavity, whereby the two entries normally are the two connections of the relevant line. But the new method can also be carried out in such a manner that the intensity distributions of light beams emanating from the cavities are recorded on that same point of entry into which the light beams have been directed. This may be useful in individual cases where the cavity has several entries. Execution of the method in this manner is, however, necessary if there is only one entry.

If several entries are provided, it must be ensured that defined conditions are present at the exits which are not used for directing light beams or for recording emanating light beams. Light traps, for example, can be arranged at these entries. But it is also possible to place a mirror in front of these entries.

To simplify matters, the intensity distributions of light beams emanating from the cavities can be recorded in one plane. In principle, it is equally possible to record the intensity distributions at the interior side of a spherical shell, surrounding the relevant entry. But this is far more complicated and does not result in any technical advantages.

The new method can for example be carried out by directing a bundle of light beams, originating from a point light source, into the cavity, the light beams being distributed evenly over the entry to the cavities and having equal intensities each.

However, adaptation of the defined intensities of light beams directed into the cavities to the relevant cavities to be tested is preferred. Such adaptation can be effected by means of a screen, which covers part of the light beams emanating from a light source, since these do not deliver significant intensity values for the recorded intensities of the beams emanating from the cavities and/or only result in an increased baseline for the relevant emanating light beams. Instead of a screen, a partitioned filter or similar apparatus can be used for adaptation of the defined intensities to the relevant cavities to be tested.

Superimposition of the intensities of different light beams emanating from the cavities can also be prevented by swinging and/or shifting a single light beam for applying light beams with the defined intensities. Swinging and/or shifting the single light beam is carried out opposite to the relevant entry to the cavity, into which the light beams are directed. It is a matter of course that superimposition of the light beams emanating from the cavities can only be prevented if their intensity distributions are recorded with respect to time.

Comparison of the intensity distribution of a cavity to be tested with the standard distribution can be evaluated in such a manner that each cavity to be tested is rejected, if the intensity distribution of light beams emanating from the cavity shows a deviation from the standard distribution, which exceeds a limit value in certain areas, is rejected. The relevant areas and the limit value are to be adapted to the cavities to be tested and to the requirements, whose fulfilment is to be observed by means of the test.

Comparison of the relevant intensity distribution with the standard distribution can also be evaluated in a more differentiated manner in order to, for example, carry out specified rework of the cavities.

In the new method, the light beams directed into the cavities have preferably light beams of visible light. The exact wavelength is to be adapted to the cavities to be tested.

An apparatus for testing open but not completely visible cavities on the basis of the method according to the invention has a light source for directing light beams with defined intensities into cavities, a locally resolving, large-surface photoelectric detector for recording intensity distributions of light beams emanating from the cavities, a memory for storing at least one recorded intensity distribution as a standard distribution and an evaluation apparatus for comparing recorded intensity distributions with the standard distribution.

BRIEF DESCRIPTION OF THE DRAWINGS

In the drawings:

FIG. 1 shows testing a cavity in a line section with a 180° bend,

FIG. 2 shows testing a sack-shaped, not completely visible cavity and

FIG. 3 shows testing a cavity with an annular cavity and two radial branch lines.

DETAILED DESCRIPTION OF THE PREFERRED EMBODIMENTS

A line section 1, which is presented in FIG. 1 in a longitudinal cross section, surrounds a cavity 2, which is not completely visible from entries 3 and 4 of the line section 1. For testing the cavity 2 in the line section 1, light beams 5 are directed into the cavity 2 at the entry 3. The light beams 5 are a divergent light beam cluster 6, which is obtained by diverging a laser beam 8, emanating from a laser 7, with a lens 9. An individual light beam, which course through the cavity 2 is indicated in detail, is provided with reference sign 5. The light beam 5 is reflected several times at a wall 10 of the cavity 2, until it finally emanates from the entry 4 of the cavity 2 in the line section 1. There, it reaches a photoelectric detector 11. The photoelectric detector 11 records an intensity distribution of all the light beams 5 of the light beam cluster 6, emanating from the cavity 2. Since these light beams have passed through the non visible areas of the cavity 2, they carry information about these areas. This information is utilized by recording the intensities of the emanating light beams 5. For testing the cavity 2, the intensity distribution of the emanating light beams 5 is first recorded with a standardized line section 1 having a standardized cavity 2 by using photoelectric detector 11, and the intensity distribution is saved as a standard distribution in a memory 12. Subsequently, the light beams 5 are with equal intensities directed into the cavities 2 to be tested of line sections 1 to be tested, and the intensity distributions of the light beams 5 emanating from said cavities 2 are recorded by the photoelectric detector 11. These intensity distributions are compared by an evaluation apparatus 13 with the standard distribution stored in the memory 12. The comparison allows statements to be made about possible deviations of the cavities to be tested from the standardized cavity. In case of certain deviations, the line sections 1 are to be rejected or reworked.

A vessel 14, which is presented in FIG. 2, has only one entry 3 to cavity 2 in its interior. For executing the new method, the light beams 5 must be directed into the same entry 3 where the light beams 5 emanating from the cavity 2 are also recorded. For this purpose, a beam divider 15 has been arranged in front of the entry 3. Behind the beam divider 15, the laser 7 with the lens 9 has been provided; whereas the photoelectric detector 11 has been arranged at the side of the beam divider 15. The light beam 5, shown in FIG. 2, documents as to how the light beam 5 also reaches those areas, which are not directly visible from the entry 3 by means of reflections on the wall 10 of the vessel 14. The light beam 5 obtains information from these areas, which are evaluated through recording its intensity by the photoelectric detector subsequent to emanation from the cavity 2. The principle method of testing the vessel 14 on the basis of the structure according to FIG. 2 corresponds with the procedure already described with regard to FIG. 1.

The same applies to testing workpieces 16, presented in FIG. 3, one of which is shown in cross section. In accordance with FIG. 3, however, the light beams 5, which are with defined intensity distribution directed into the cavity 2, are generated in another way than in FIGS. 1 and 2. Instead of a lens, positioned in front of laser 7, means have been provided for swinging laser 7 in the direction of an arrow 17 and also vertically. In each position of the laser 7, laser beam 8 forms one light beam 5 of a light beam cluster. In synchronization with swinging laser 7, the intensity distributions of the light beams 5 emanating from the cavity 2 are recorded by the photoelectric detector 11. This means that the standard distribution stored in the memory 12 for the standardized cavity 2 is a sequence of two-dimensional intensity distributions with respect to time. Such two-dimensional intensity distributions with respect to time are also recorded for the cavities to be tested 2 and compared with the standard distribution. The cavity 2, inscribed in workpiece 16, has a relatively complicated structure. It has an annular cavity 18 and two radial branch lines 19, which lead to the entries 3 and 4 of the cavity 2. With the new method sufficiently detailed testing of such complicated cavities 2 for deviations from standardized cavities is also possible.

We claim:

1. A method of testing open but not completely visible cavities having at least one entrance, comprising the steps of
   directing light beams with a defined spatial light intensity distribution into one entrance of a standardized cavity from outside the cavity,
   recording a spatial light intensity distribution of light beams emanating from one entrance of the standardized cavity to the outside of the cavity and saving the spatial light intensity distribution as a standard distribution,
   directing the light beams with the defined spatial light intensity distribution into one entrance of the cavity to be tested from outside the cavity,
   recording the spatial light intensity distribution of light beams emanating from one entrance of the cavity to be tested to the outside of the cavity, and comparing the recorded spatial light intensity distributions with the standard distribution.

2. The method of claim 1, wherein, in the steps of directing the light beams with the defined spatial light intensity distribution into the standardized cavity and into the cavities to be tested, the light beams are divergent relative to each other.

3. The method of claim 1, wherein, in the steps of recording the spatial light intensity distribution of light beams emanating from the standardized cavity and from the cavities to be tested, the spatial light intensity distributions of light beams are recorded at another entrance into the cavity than the entrance where the light beams are directed into the cavity.

4. The method of claim 1, wherein, in the steps of recording the spatial light intensity distribution of light beams emanating from the standardized cavity and from the cavities to be tested, the intensity distributions of the light beams emanating from the cavities are recorded in one plane.

5. The method of claim 1, wherein, in the steps of directing the light beams with the defined spatial light intensity distribution into the standardized cavity and into the cavities to be tested, the defined spatial light intensity distribution of the light beams are adapted to the cavities to be tested.

6. The method of claim 1, wherein, in the steps of directing the light beams with the defined spatial light intensity distribution into the standardized cavity and into the cavities to be tested, a single light beam is shifted for providing the light beams with the defined spatial light intensity distribution.

7. The method of claim 6, wherein, in the steps of recording the spatial light intensity distribution of light beams emanating from the standardized cavity and from the cavities to be tested, the spatial light intensity distributions of the light beams emanating from the cavities are recorded with respect to time.

8. The method of claim 1, further comprising the step of rejecting each cavity to be tested, in which the spatial light intensity distribution of the emanating light beams shows a deviation from the standard distribution that exceeds a limit value in certain areas.

9. The method of claim 1, wherein, in the steps of directing the light beams with the defined spatial light intensity distribution into the standardized cavity and into the cavities to be tested, the light beams have wavelengths of visible light.

10. A method of testing open but not completely visible cavities comprising the steps of:

(a) selecting one of the cavities as a standardized cavity;

(b) directing a bundle of light beams with a known intensity distribution into one opening of the standardized cavity from outside the cavity;

(c) detecting an intensity distribution of light beams emanating from one opening of the standardized cavity to the outside of the cavity and recording the detected intensity distribution as a standardized distribution;

(d) selecting one of the cavities to be tested;

(e) directing the bundle of light beams with the known intensity distribution into one opening of the cavity to be tested from outside the cavity;

(f) detecting an intensity distribution of light beams emanating from one opening of the cavity to be tested to the outside of the cavity;

(g) comparing the detected intensity distribution of light beams emanating from the one opening of the cavity to be tested to the standardized distribution; and (h) making conclusions about the tested cavity based upon the results of the comparison.

11. The method of claim 10 and wherein the cavities each have one opening and wherein the light beams are directed into the one opening and detected as they emanate from the one opening.

12. The method of claim 10 and wherein the cavities have at least two openings and wherein the light beams are directed into one of the openings and detected as they emanate from another opening.

13. The method of claim 10 and where in steps (b) and (e), the light beams directed into the opening are divergent relative to each other.

14. The method of claim 13 and wherein the divergent light beams are directed into the opening simultaneously.

15. The method of claim 13 and wherein the divergent light beams are directed into the opening sequentially over time and wherein steps (c) and (f) comprise detecting the emanating light beams sequentially over time.

16. The method of claim 10 and where in steps (b) and (e), the known intensity distribution is a spatial light intensity distribution.

17. The method of claim 16 and where in steps (c) and (f), the detected intensity distribution is a spatial light intensity distribution.

18. The method of claim 10 and where in steps (c) and (f), the light beams emanating from an opening of the cavities are detected in a plane.

19. The method of claim 10 and wherein step (h) comprises rejecting the tested cavity if the differences between the standardized distribution and the detected intensity distribution from the tested cavity exceed a predetermined threshold.

* * * * *